(12) United States Patent
Yee (10) Patent No.: US 7,300,151 B2
(45) Date of Patent: Nov. 27, 2007

(54) APPARATUS AND METHOD FOR EYE COMFORT (75) Inventor: Richard Yee, Houston, TX (US)

(73) Assignee: SeeFit Incorporated, Houston, TX (US)

( * ) Notice: Subject to any disclaimer, the term of this patent is extended or adjusted under 35 U.S.C. 154(b) by 0 days.

(21) Appl. No.: 11/216,602

(22) Filed: Aug. 30, 2005

(65) Prior Publication Data
US 2006/0055878 A1   Mar. 16, 2006

Related U.S. Application Data (60) Provisional application No. 60/605,713, filed on Aug. 30, 2004, provisional application No. 60/633,915, filed on Dec. 7, 2004.

(51) Int. Cl.
G02C 7/02 (2006.01)
(52) U.S. Cl. .................. 351/159; 351/62; 351/177; 2/428
(58) Field of Classification Search ................ 351/159, 351/62; 2/428
See application file for complete search history.

(56) References Cited

U.S. PATENT DOCUMENTS

| 4,934,807 | A | * | 6/1990 | Bolle et al. ............ 351/62 |
| 5,428,411 | A | * | 6/1995 | Kopfer ................. 351/62 |
| 5,631,717 | A | * | 5/1997 | Spector ............... 351/44 |
| 6,009,564 | A | * | 1/2000 | Tackles et al. .......... 2/436 |
| D428,913 | S | | 8/2000 | Kopfer |
| 6,210,000 | B1 | | 4/2001 | Yee |
| 6,233,342 | B1 | | 5/2001 | Fernandez |
| 6,270,467 | B1 | | 8/2001 | Yee |
| 6,386,701 | B1 | | 5/2002 | Khulusi |
| 6,550,914 | B1 | | 4/2003 | Kopfer |
| D481,064 | S | | 10/2003 | Fernandez et al. |
| 6,641,263 | B2 | | 11/2003 | Olney |
| 6,641,264 | B1 | | 11/2003 | Schwebel |
| 6,874,884 | B2 | | 4/2005 | Schwebel |
| 6,886,933 | B2 | | 5/2005 | Schwebel |
| 6,908,195 | B2 | | 6/2005 | Fuller |
| 6,994,433 | B2 | * | 2/2006 | Hockaday et al. ........... 351/62 |
| 2002/0116750 | A1 | | 8/2002 | Korb |
| 2003/0081169 | A1 | | 5/2003 | Kopfer |
| 2003/0193644 | A1 | | 10/2003 | Schwebel |

(Continued)

OTHER PUBLICATIONS

"Melaoptix Computer Glasses," Sep. 8, 2005, http://shop.store.yahoo.com/kitchenhome/mecogl.html, My Kitchen & Home, p. 1.

(Continued)

Primary Examiner—Jordan M. Schwartz
(74) Attorney, Agent, or Firm—Chowdhury & Georgakis, P.C.

(57) ABSTRACT

An apparatus and method for preventing ocular surface abnormalities. This apparatus includes a frame containing at least one lens and at least one seal. The frame, lens, and seal provide an area about the eyes of a user that is at least partially enclosed from a surrounding environment when worn. Humidity and temperature are increased in the area about the eyes of the user to provide a microenvironment in the area about the eyes of the user. The microenvironment is capable of reducing or preventing ocular surface abnormalities, alleviating ocular discomfort, and improving ocular health. The seal may be removable and may attach to prescription eyeglasses, sunglasses, and so on. The seal may also contain a filter, such as a HEPA filter.

21 Claims, 6 Drawing Sheets

U.S. PATENT DOCUMENTS

2005/0022823 A1    2/2005   Davison et al.
2006/0126008 A1*   6/2006   Olney ......................... 351/62
2006/0139569 A1*   6/2006   Schwebel .................... 351/62

OTHER PUBLICATIONS

"Suma Brand Inventions for the New Millenium," Sep. 8, 2005, http://www.sumabrand.com/, Suma Brand, pp. 1-3.

"Panoptx—Dry Eye Syndrome," Aug. 12, 2005, http://www.panoptx.com/html/dry_eye_syndrome.htm, Panoptx, pp. 1-7.

Clayton, Blehm, Seema, Vishnu, Ashbala Khattak, Shrabanee Mitra, and Richard Yee, "Computer Vision Syndrome: A Review," Survey of Ophthalmology, May-Jun. 2005, pp. 253-262, vol. 50, issue 3.

Kevin Dawson and Richard Yee, "Phase 2 Research Plan Dec. 1, 2004," Dec. 1, 2004, pp. 15-34.

Theresa Gan, Kevin Dawson, Alice Chuang, and Richard Yee, "Comparing Periocular Humidity in Different Types of Eyewear," May 2004, pp. 1-6.

Donald Korb, Jack Greiner, Thomas Glonek, Roya Esbah, Victor Finnemore, Amy Whalen, "Effect of Periocular Humidity on the Tear Film Lipid Layer," Cornea, 1996, pp. 129-134, vol. 15, issue 2, Lippincott-Raven Publishers, Philadelphia, U.S.A.

Kazuo Tsubota, "The Effect of Wearing Spectacles on the Humidity of the Eye," American Journal of Ophthalmology, Jul. 1989, pp. 92-93, vol. 108, issue 1.

* cited by examiner

APPARATUS AND METHOD FOR EYE COMFORT

This application claims priority under 35 USC §119(e)(1) of Provisional Application No. 60/605,713, filed Aug. 30, 2004, and Provisional Application No. 60/633,915, filed Dec. 7, 2004, both incorporated herein by reference.

TECHNICAL FIELD OF THE INVENTION

The present invention relates to maintaining or improving eye health and comfort. Still more particularly, the present invention relates to maintaining or improving eye health by creating a microenvironment around a user's eyes.

BACKGROUND OF THE INVENTION

Discomfort in an around the surface of the eyes, known as ocular surface discomfort, is an undesirable and irritating affliction affecting many people. Such discomfort can result in loss of productivity, distraction, and unhappiness in sufferers. Ocular surface discomfort may result from dry eyes, lack of blinking the eye, computer vision syndrome (CVS), allergies, airborne eye irritants, environmental factors, and so on.

Dry eyes occur when tears generated by glands near the eye are not of the correct quality or quantity to lubricate the eye. Dry eyes can be caused by problems in the eye and the eye's surrounding glands or a lack of blinking the eye. Symptoms of dry eyes include dryness, stinging, burning, scratchiness, redness, and a gritty feeling on the surface of the eye.

Lack of blinking the eye generally occurs when a person is attentive and concentrating on a task. For example, a person is attentive and concentrating on a task when they are working at a computer, reading, driving, watching a television or theater screen, looking through a microscope, and so on. A lack of blinking prevents lubricating tear film, a layer of fluid that bathes and lubricates the eye, from spreading across the surface of the eye, which may result in the dry eye symptoms describe above. Allergens, airborne eye irritants, and other environmental factors may also cause ocular discomfort.

Computer vision syndrome refers to a condition in which a person experiences one or more ocular symptoms resulting from operation of a computer and looking at a computer screen. CVS may be caused by a lack of blinking the eye while looking at a computer screen. CVS may also occur because of an increase in ocular surface area exposed to evaporation while looking at a computer screen. For example, more ocular surface area is exposed to evaporation when viewing a computer screen than in a reading position. An increase in the ocular surface area exposed to evaporation may alter the tear film in the eye, thus leading to ocular discomfort. Symptoms of CVS include eyestrain or eye fatigue, dry eyes, burning eyes, sensitivity to light, blurred vision, headaches, and pain in the shoulders, back, or neck.

As described above, ocular surface discomfort has many sources and many symptoms. A device that relieves or prevents sources or symptoms of eye discomfort and protects the eye from environmental factors would be desirable.

SUMMARY OF THE INVENTION

The problems noted above are solved by providing an area about the eyes of a user that is at least partially enclosed from a surrounding environment and providing humidity in the area about the eyes of the user to make the eyes comfortable. Additionally, temperature in the area about the eyes of the user that is at least partially enclosed may be increased. The area about the eyes of the user that is at least partially enclosed from the surrounding environment comprises a frame, at least one lens attached to the frame, and at least one seal attached to the frame. The frame may be an eyeglasses frame. The frame contains at least one lens aperture and has a front face and a rear face. The rear face is proximate to the user's eyes when the frame is worn by the user. The at least one lens is disposed in each lens aperture of the frame. The seal extends from the frame in the general direction of the eyes of the user and in the direction of the rear face of the frame.

The frame, at least one lens, and at least one seal attached to the frame are capable of providing humidity and increasing temperature in an area between the eyes of the user and the at least one lens aperture. The frame, at least one lens, and at least one seal may be used for an outdoor activity, watching a screen, construction work, driving a vehicle, riding a bicycle, participating in a sport, working in a laboratory work, riding in a vehicle, or any activity in which a reduced rate of blinking occurs. The frame, at least one lens, and at least one seal may form a seal around the user's eyes.

The area between the eyes of the user and the at least one lens aperture that is at least partially enclosed from the surrounding environment is a microenvironment. The microenvironment may be capable of reducing surface abnormalities in the eyes of the user, reducing dryness in the eyes of the user, reducing computer vision syndrome in the eyes of the user, reducing ocular discomfort, or improving ocular health. The microenvironment may alleviate symptoms associated with dry eyes, blepharitis, computer vision syndrome, lack of blinking, allergies, eye irritants, and so on. In some embodiments of the invention, the user may be reminded to blink to improve ocular health.

In some embodiments of the invention, the at least one seal is removable and detachable from the frame. The seal may attach to at least a portion of the frame. The frame, at least one seal, and at least one lens are capable of increasing humidity and increasing temperature in the area between the eyes of the user and the at least one lens aperture. The at least one seal may attach to the frame by at least one screw, at least one latch, or at least one clamp. The at least one seal may be a gasket.

In some embodiments of the invention, a filter may attach to the frame, the at least one lens, or the at least one seal. The filter may be removable and may be a high efficiency particle air (HEPA) filter. The filter may filter at least some atmosphere entering or exiting the area about the eyes of the user. The filter may also prevent a source of disease from entering the area about the eyes of the user that is at least partially enclosed from the surrounding environment.

The at least one lens may provide the user a transparent or semitransparent line of sight through the area about the eyes of the user that is at least partially enclosed from the surrounding environment. The line of sight may correct the user's vision using the at least one lens. The at least one lens may be transparent, semitransparent, tinted, polarized, or operable to filter at least one wavelength of light. A defogging agent may be applied to the at least one lens.

The seal may contain material capable of increasing temperature in the area between the eyes of the user and the at least one lens aperture. For example, the at least one seal may be plastic, rubber, silicone, foam, leather, or pliable metal. The at least one seal may be a permeable, semipermeable, or nonpermeable material. The seal may contain a flexible wall having an attachment end and an opposing sealing end. The attachment end is attaches to the frame. The flexible wall extends from the frame in the direction of the rear face of the frame. The flexible wall and the at least one sealing end are adapted to abut the user's face when worn. The flexible wall may be linear or an accordion-like shape between its attachment end and sealing end.

In some embodiments of the invention, a nosepiece may attach to the frame proximal to the user's nose when worn. The frame, at least one lens, at least one seal, and the nosepiece may form a seal around the user's eyes.

BRIEF DESCRIPTION OF THE DRAWINGS

The embodiments of the invention will now be described with reference to the accompanying drawings in which:

FIG. 6, in accordance with some embodiments of the invention, shows a top view of the eyeglasses shown in FIG. 4;

FIG. 13, in accordance with some embodiments of the invention, shows a top view of eyeglasses shown in FIG. 11.

NOTATION AND NOMENCLATURE

Certain terms are used throughout the following description and claims to refer to particular system components and configurations. As one skilled in the art will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ". Also, the term "attach" or "attaches" is intended to mean either an indirect or direct physical connection. Thus, if a first component is attached to a second component, that connection may be through a direct physical connection or through an indirect physical connection via other components and connections.

DETAILED DESCRIPTION OF PREFERRED EMBODIMENTS

In accordance with some embodiments of the invention, an apparatus is described to prevent ocular surface discomfort and abnormalities in human eyes. The apparatus may be eyeglasses containing a frame, at least one lens, and at least one seal. The frame, at least one lens, and at least one seal provide an area about the eyes that is at least partially enclosed from a surrounding environment when the eyeglasses are worn. Humidity and temperature are maintained or increased in a microenvironment in the area about the eye. Thus, the microenvironment is capable of reducing or preventing symptoms and sources of ocular surface discomfort and abnormalities, such as dry eyes, computer vision syndrome, lack of blinking the eye, and so on.

Figure 1A:
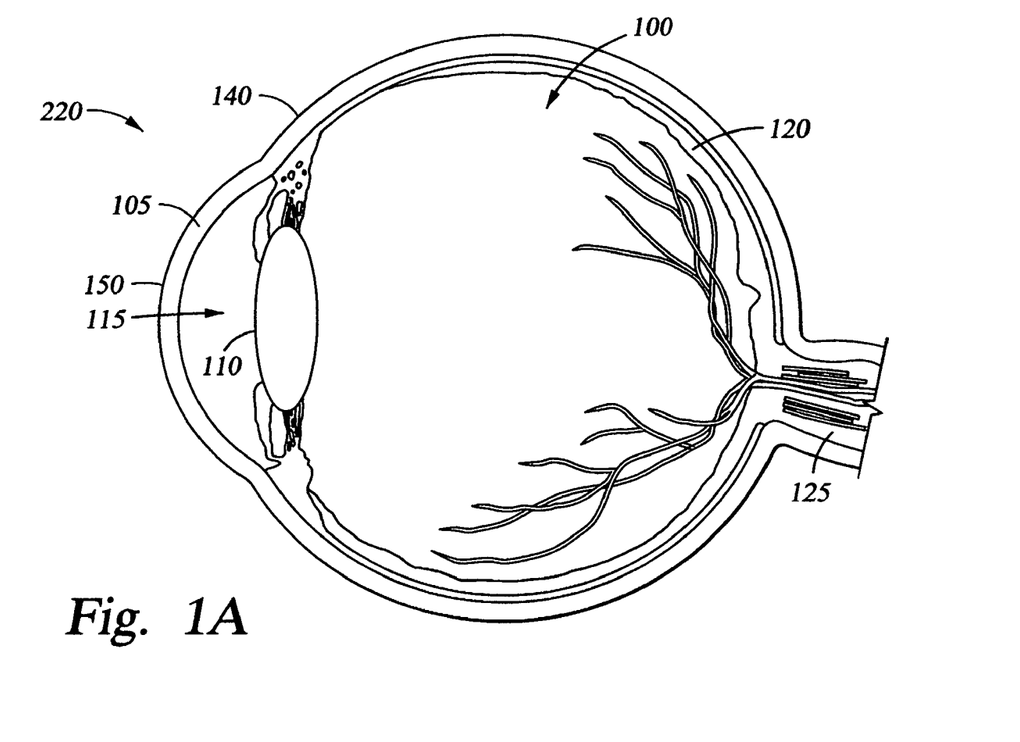
FIG. 1a shows a vertical cross section of a human eye.
Figure 1B:
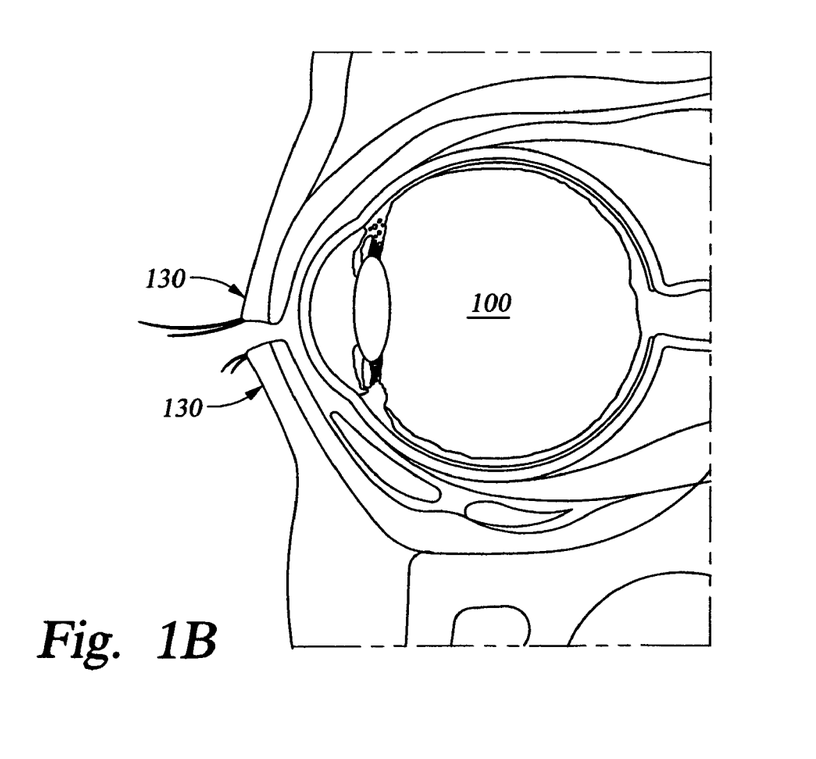
FIG. 1b shows a vertical cross section of a human eye including an eyelid.

Referring to FIGS. 1a and 1b, an illustration of a human eye 100 is shown. A cornea 105 and lens 110 focus light entering eye 100 through a pupil 115 onto a retina 120. Light hitting the retina sends impulses through an optic nerve 125 to a brain (not show in FIGS. 1a and 1b). An eyelid 130 (shown in FIG. 1b) is capable of wiping away impurities from an ocular surface 150 that is the outside surface of cornea 105 exposed to an atmosphere 220 external to eye 100. Eyelid 130 also prevents eye 100 from dehydration by spreading a tear film, described in more detail below, over the ocular surface 150.

Figure 2:
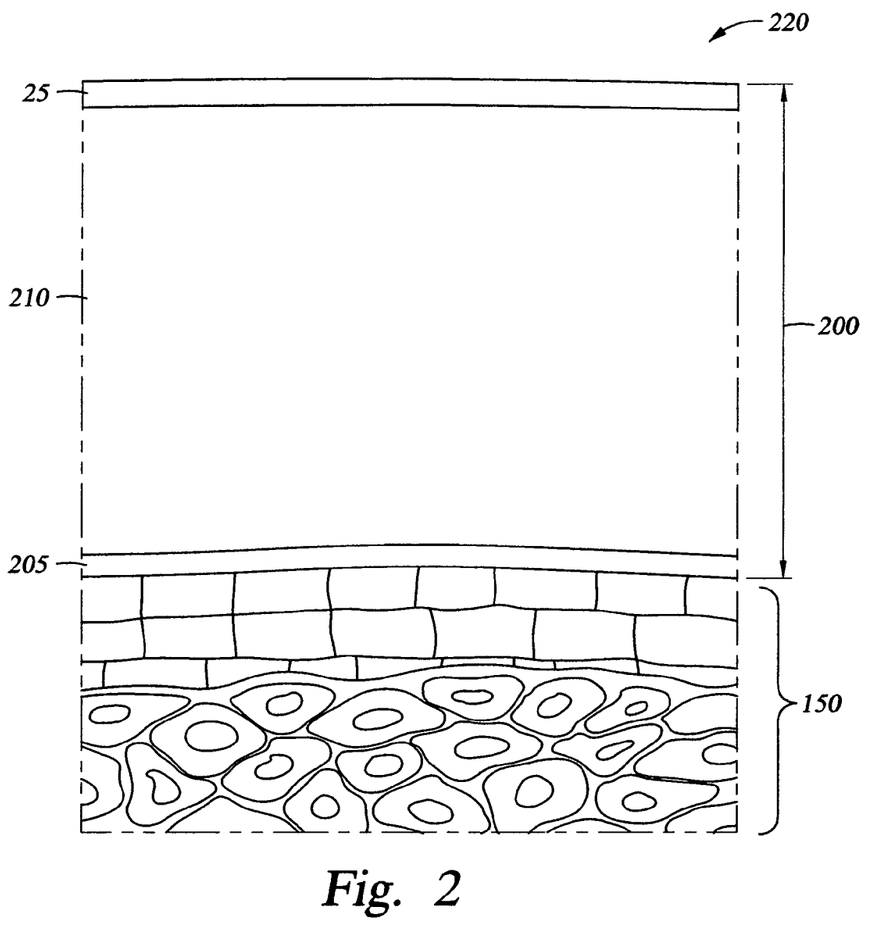
FIG. 2 shows a tear film on an ocular surface.

Turning now to FIG. 2, tear film 200 includes a mucin layer 205, an aqueous gel layer 210, and a lipid layer 25. The mucin layer 205 is located on ocular surface 150 and serves to spread the aqueous gel layer 210 evenly over the ocular surface 150 and the remaining surface of the eye known as the conjunctiva 140 (shown in FIG. 1a). Mucin layer 205 also coats small foreign bodies, such as dust or debris, so they can be easily removed by blinking of eyelid 130.

Aqueous gel layer 210 consists of a dilute solution of salts, minerals, and dissolved organic materials. This layer represents approximately 90% of the thickness of tear film 200. Furthermore, aqueous gel layer 210 hydrates ocular surface 150 and flushes contaminants from eye 100. Lipid layer 25 contains components secreted by glands (not shown in FIG. 2) near eye 100. The components in lipid layer 25 serve as a barrier against tear evaporation into atmosphere 220. Lipid layer 214 also provides lubrication to ocular surface 150.

Figure 3:
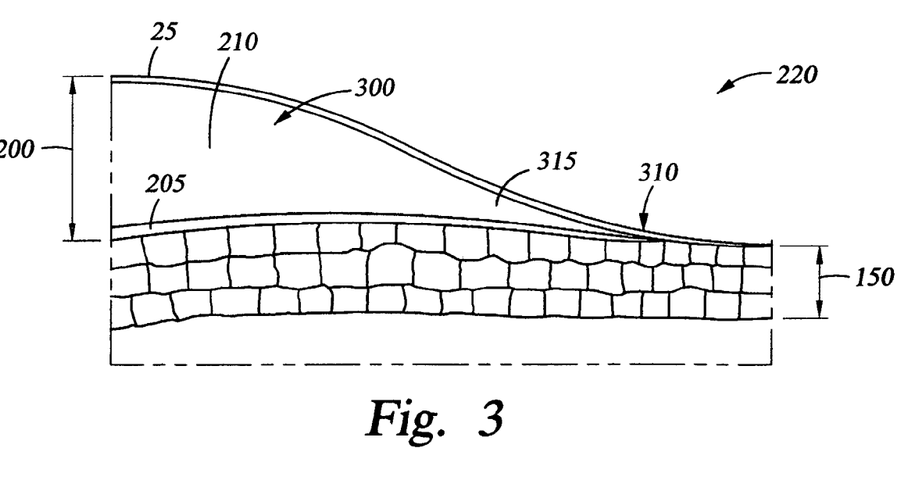
FIG. 3 shows an adequate tear film and a dry spot on an ocular surface.

Turning now to FIG. 3, an adequate tear film 300 and a dry spot 310 on eye 100 are shown. Adequate tear film 300 contains a thick aqueous gel layer 210 similar to tear film 200 shown in detail in FIG. 2. Dry spot 310 contains a thin aqueous gel layer 315. Dry spot 310 may be considered an inadequate tear film because the dry spot fails to offer the degree of protection, hydration, or lubrication adequate tear film 300 offers. Thus, a patient with dry spot 310 in eye 100 may experience dryness, stinging, burning, scratchiness, or a gritty feeling on ocular surface 150. Dry spot 310 may be caused by evaporation of aqueous gel layer 315.

Ocular surface abnormalities may be caused by an inadequate tear film, such as the tear film shown in FIG. 3. Environmental factors, such as dry air, ventilation fans, static buildup, dust, and airborne contaminants may also contribute to ocular surface abnormalities. Additionally, increased exposure of the ocular surface 150 to the atmosphere 220, such as when a person stares forward for long periods of time when driving, using a computer, watching television, and so on, may contribute to ocular surface 150 abnormalities. Decreased blink rate while attentive or concentrating may further cause ocular surface abnormalities. Blepharitis, an inflammation of the eyelids caused by dysfunction of the meibomian gland, results in an inadequate lipid layer 25. An inadequate lipid layer 25 may lead to increased evaporation of aqueous gel layer 210 on ocular surface 150 and other ocular surface abnormalities that may result in damage to the ocular surface 150.

As described above, an abnormal ocular surface 150 may cause discomfort. This discomfort may be significant for contact lens users who rely on lubrication of the eye to allow a contact lens surface to move along ocular surface 150 with minimal resistance. Surface abnormalities, such as dry spot 310, may cause a contact lens to dry and adhere to upper eyelid 130 or ocular surface 150 during a blink by eyelid 130.

Figure 4:
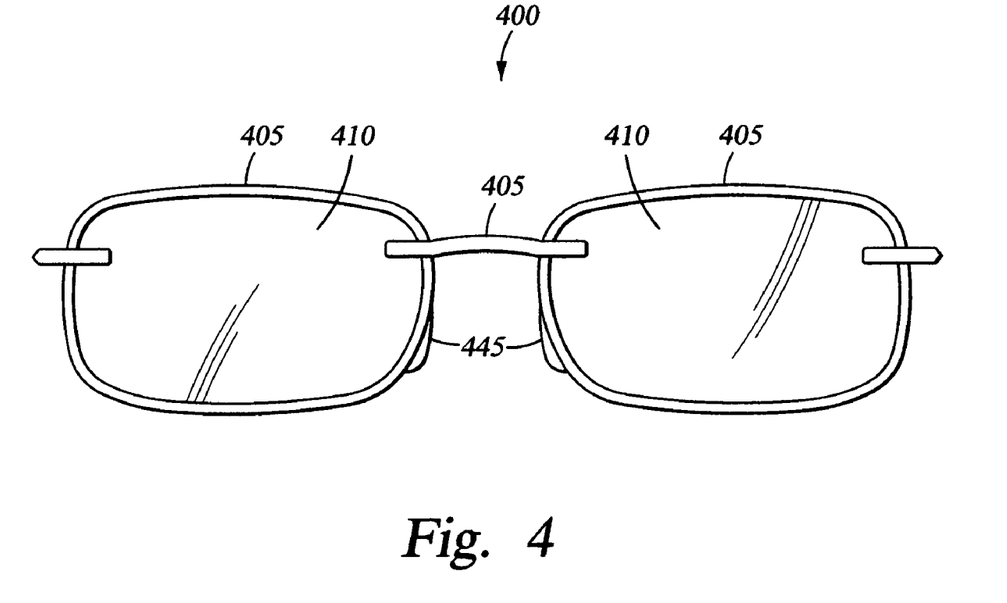
FIG. 4, in accordance with some embodiments of the invention, shows a front view of eyeglasses.
Figure 5:
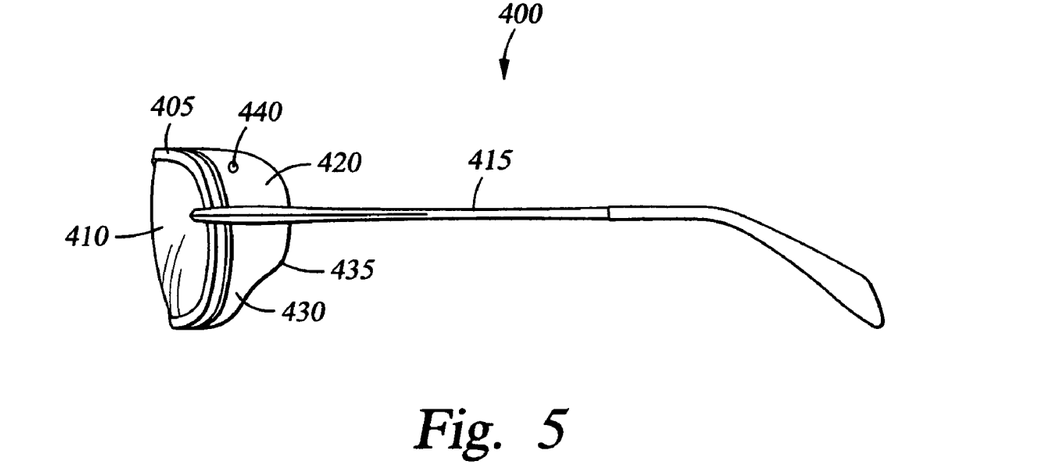
FIG. 5, in accordance with some embodiments of the invention, shows a side view of the eyeglasses shown in FIG. 4.
Figure 6:
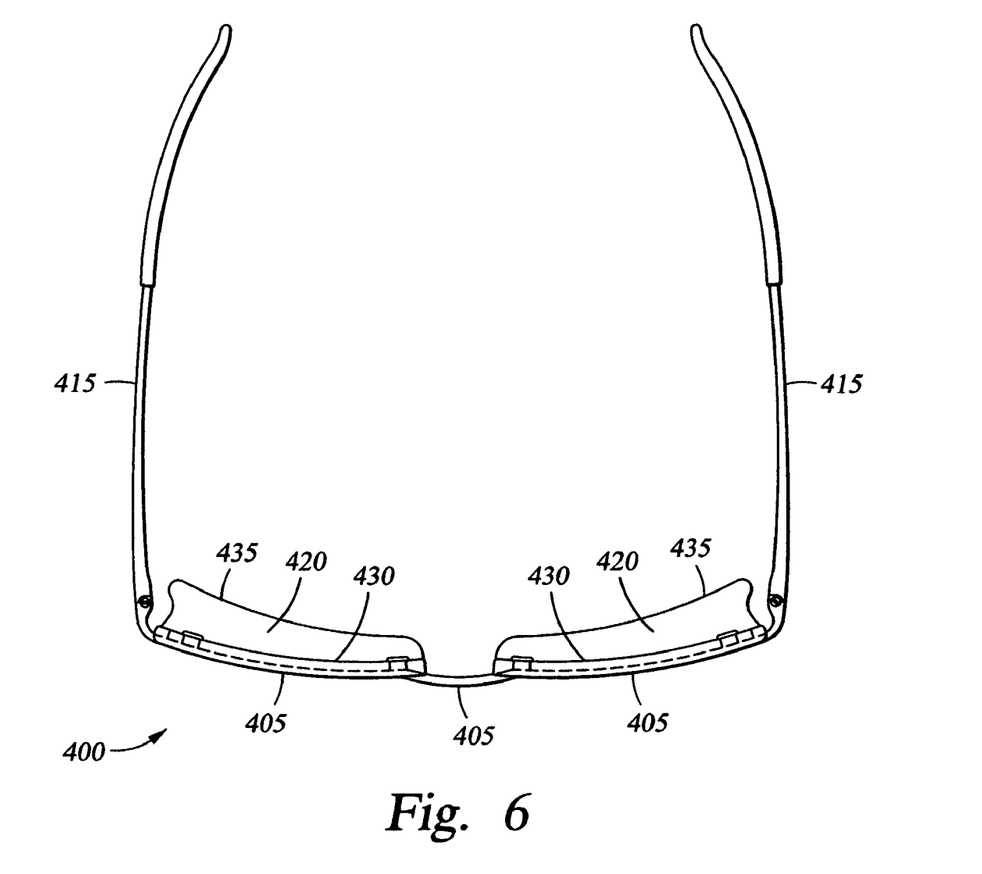

FIGS. 4 through 6 show a front, side, and top view of eyeglasses 400, respectively. Eyeglasses 400 include a frame 405 supporting two lenses 410. Sidearms 415 attach to frame 405 and extend away from frame 405 to support the eyeglasses 400 on a face of a user where the lenses 410 are proximate to the user's eyes. Eyeglasses 400 may be glasses used for corrective vision, safety glasses, sunglasses, lab glasses, glasses for preventing ocular surface abnormalities, and so on. Thus, lenses 410 may be corrective or non-corrective lenses, bifocal lenses, trifocal lenses, tinted lenses, polarized lenses, and so on. Lenses 410 may be glare reducing and may also filter wavelengths of light, such as certain types of ultraviolet light from a display screen or the sun. Lenses 410 may also provide magnification for a user to view small objects, such as text, diagrams, pictures, and so on.

As shown in FIG. 5, in accordance with some embodiments of the invention, a seal 420 is attached to frame 405 around each lens 410. Seal 420 extends towards a user's face when eyeglasses 400 are worn by the user. The seal 420 may be a single continuous piece and extend around each lens. Seal 420 may contain a flexible wall that has an attachment end 430 attached to frame 405 and an opposite sealing end 435. The length of seal 420 is sufficient that substantially all of sealing end 435 abuts the user's face when the eyeglasses 400 are worn by the user to form a seal. Thus, eyeglasses 400 form an enclosed area about the eyes of a user. In some embodiments of the invention, eyeglasses 400 may not completely seal to the user's face.

Seal 420 may be resilient and capable of molding to the contours of the user's face. Such resiliency and flexibility may be a function of the material properties of the flexible wall or its physical characteristics or design. Seal 420 may be made from a flexible material such as plastic, rubber, silicone, foam, leather, a thin, pliable metal, and so on. The shape of seal 420 may be adapted to provide flexibility. For example, seal 420 may have a linear shape or an accordion-like shape. Seal 420 may also be an insulator capable of maintaining or increasing temperature in the enclosed area between lenses 410, frame 405, seal 420, and the user's eyes. In some embodiments of the invention, seal 420 may be a gasket.

In some embodiments of the invention, seal 420 may be composed of material permeable, semipermeable, or non-permeable to particles. For example, in some embodiments of the invention, seal 420 may absorb moisture from the external atmosphere and retain the moisture within the enclosed area between lenses 410, frame 405, seal 420, and the user's eyes. Seal 420 may contain semipermeable material that allows some atmosphere to enter the enclosed area about the user's eyes (not shown in FIG. 5) while preventing allergens, dust, sources of disease, and so on from entering the enclosed area.

A microenvironment may occur in the enclosed area around the user's eyes between lenses 410, frame 405, and seal 420. Temperature and humidity may increase in the microenvironment in the enclosed area about the eyes of the user while the eyeglasses 400 are worn. Returning to FIG. 2, increased humidity and temperature in the microenvironment of atmosphere 220 may reduce evaporation of aqueous gel layer 210, thereby decreasing the severity and likelihood of dry spots, such as dry spot 310 in FIG. 3. Increased humidity and temperature may also increase the thickness of aqueous gel layer 210. Thus, increased temperature and humidity in the area about the eye may reduce ocular surface abnormalities, prevent ocular surface abnormalities, or reduce symptoms of ocular surface abnormalities. The increased temperature and humidity may also improve ocular health.

Returning to FIGS. 4-6, eyeglasses 400 may be used by patients who suffer from dry eyes because the microenvironment created by the eyeglasses may alleviate or prevent symptoms associated with dry eyes. Additionally, computer users, movie and television watchers, vehicle operators, passengers of a vehicle, laboratory workers, and other people performing concentrated activities may use eyeglasses 400 to reduce or remove ocular discomfort associated with a lack of blinking over a period of time. Blepharitis sufferers may also use eyeglasses 400 to reduce eye dryness and other ocular surface abnormalities. Contact lens wearers may also use eyeglasses 400 to reduce discomfort by increasing tear lubrication as described above.

In some embodiments of the invention, eyeglasses 400 may contain one more filters 440 capable of filtering atmosphere entering and exiting the enclosed area between lenses 410, frame 405, seal 420, and the area around the eyes of the user. The filter may permit the microenvironment to "breathe" by allowing atmosphere to enter and exit from the microenvironment while still maintaining humidity and temperature. The filter 440 may, for example, prevent particles that add disease to the microenvironment from entering the enclosed area about the eye. Filter 440 may prevent particles, allergens, dust, pollen, mold, pet dander, bacteria, and other airborne contaminants from entering the enclosed microenvironment. Thus, filter 440 may reduce accumulation of particles and irritants on the ocular surface, thereby decreasing frictional and foreign body irritation to the user's eyes. For example, eyeglasses 400 containing one or more filters may be worn by a user in a construction environment, manufacturing environment, industrial environment, and so on. The filter may remove airborne contaminants that may cause dryness or irritation to the user's eyes. Furthermore, eyeglasses 400 may be used for outdoor activities, such as hiking, participating or watching a sport, and so on.

Filter 440 may be a high efficiency particle air (HEPA) filter or the like including filter cartridges that may be easily replaced. As shown in FIG. 5, filters 440 may be located in seal 420 operable to filter each enclosed area. In some other embodiments of the invention, filters may also be located in lenses 410 or frame 405. In some embodiments of the invention, the filters may be removable. Thus, for example, each filter located in a filter gap may be removed and replaced with one or more covers capable of closing the filter gap and sealing the enclosed area between lenses 410, frame 405, seal 420, and the user. In some other embodiments of the invention, the filters may removable, thus allowing a small open gap path between the external environment and the enclosed area between lenses 410, frame 405, seal 420, and the user. While the open filter gap may decrease the temperature and humidity in the enclosed area, eyeglasses 400 may still be capable of relieving or preventing ocular surface abnormalities.

Filter 440 may prevent allergens and airborne particles, such as sand, dust, and so on, from entering a user's eye. The filters may also allow air to enter and exit the enclosed area at a controlled rate. This may reduce fogging in lenses 410 when eyeglasses 400 are worn. In some embodiments of the invention, to prevent fogging when eyeglasses 400 are worn, lenses 410 may be treated with an antifogging agent.

In some embodiments of the invention, a pair of nose pads 445 may attach to frame 405 and support or partially support eyeglasses 400 on the user's face. The pair of nose pads may be a nose bridge operable to support or partially support eyeglasses 400 on the user's face. Nose pads 445 may be customizable to properly fit eyeglasses 400 to the user's face. For example, the user may choose from an assortment of nose pads 445 to achieve a desirable and enclosing fit for eyeglasses 400. Further, nose pads 445 may or may not contribute to the enclosed area about the user's eyes. Thus, the enclosed area may be between lenses 410, frame 405, seal 420, nose pads, and the user. In some embodiments of the invention, the enclosed area may not include nose pads 445. In some other embodiments of the invention, eyeglasses 400 may not include nose pads 445; frame 405 and seal 420 may support eyeglasses 400 on the user's face.

Eyeglasses 400 may be further customizable. For example, frame 405 may bend to customize the eyeglasses 400 to a user's face. Sun shades may be attached to frame 405 to cover lenses 410. Additionally, seal 420 may be configured to remove glare from indirect light sources, such as ceiling lights or sunlight through a window, thus reducing discomfort for the user. However, in some embodiments of the invention, seal 420 may be configured to allow uninhibited or moderately uninhibited peripheral vision for a user.

Eyeglasses 400 may also prevent ocular surface abnormalities caused by drafts and air turbulence. Thus, for example, a person in a drafty room may wear eyeglasses 400 to prevent air drafts from causing dry spots in their eyes or causing other ocular surface abnormalities. Eyeglasses 400 may also be used in an airplane to increase humidity about the eye and prevent drafts from causing ocular surface abnormalities. Additionally, eyeglasses 400 may be used for outdoor activities such as skiing, biking, cycling, motorcycle riding, hang gliding, hiking, riding in a vehicle and other activities in which wind, currents of air, airborne particles, and so on may induce eye discomfort.

Figure 7:
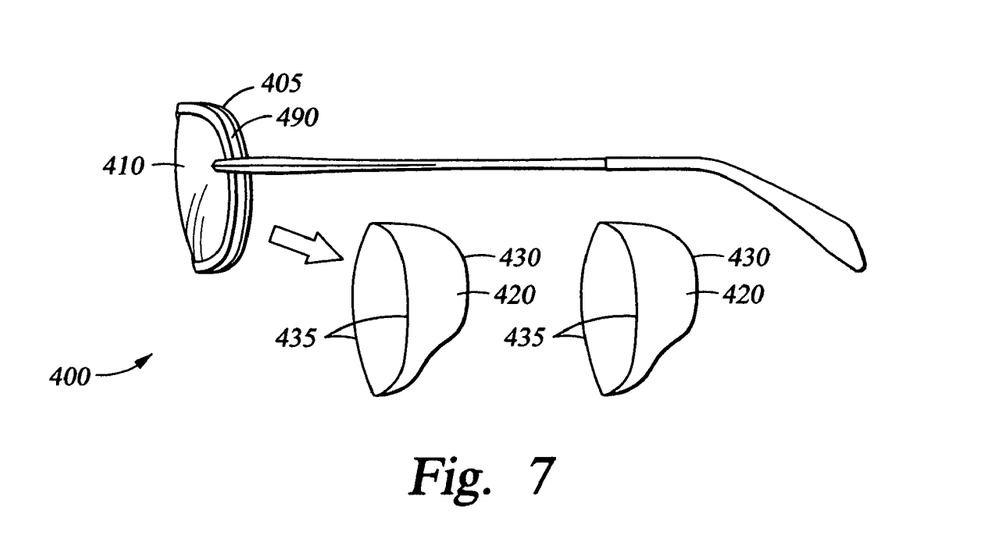
FIG. 7, in accordance with some embodiments of the invention, shows a side view of the eyeglasses shown in FIG. 4 containing removable seals.
Figure 8:
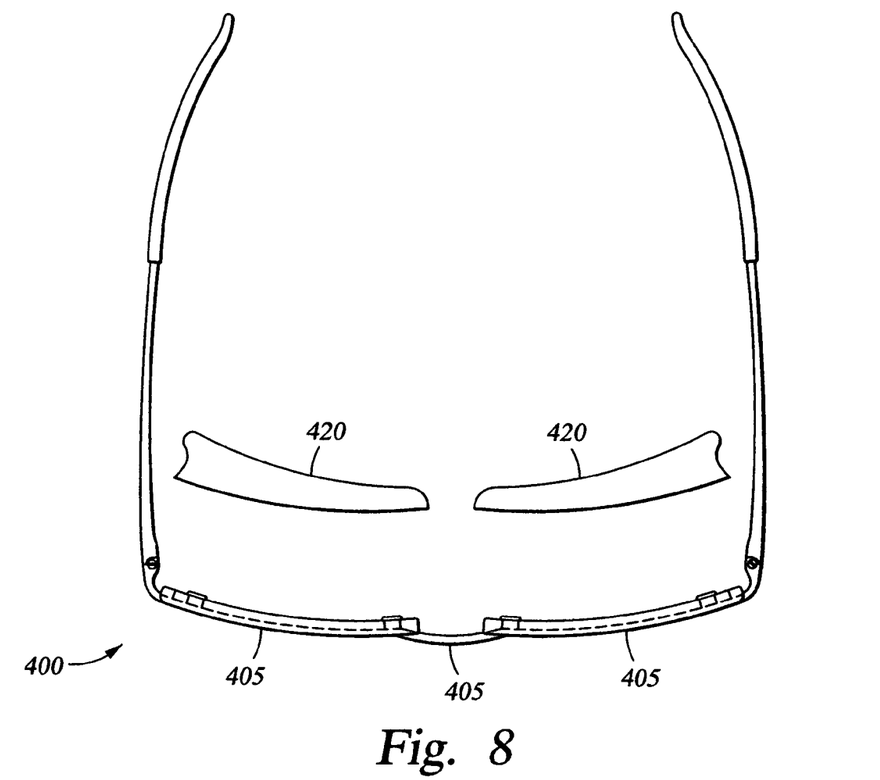
FIG. 8, in accordance with some embodiments of the invention, shows a top view of the eyeglasses containing removable seals shown in FIG. 7.

FIGS. 7 and 8 show a top and side view of eyeglasses 400 where seal 420 is removable from frame 405 in accordance with some embodiments of the invention. A front view of eyeglasses 400 resembles the front view of eyeglasses 400 shown in FIG. 4. For instance, a user may attach seals 420 to frame 405 when working outside in an environment containing airborne allergens. Each seal 420 may attach to frame 405 using one or more screws, one or more clamps, one of more latches, and so on. Eyeglasses 400 may contain prescription lenses 410 to correct the user's vision. The user may remove seals 420 to read a novel at home, attend a dinner, or perform an activity in which a microenvironment may not be necessary. Additionally, a user who suffers from computer vision syndrome may use eyeglasses 400 when viewing a computer screen. The user may remove seals 420 from eyeglasses 400 when no longer viewing the computer screen. In some embodiments of the invention, a dry eye sufferer may experience dry eye symptoms while watching a movie. The dry eye suffered may attach seals 420 to eyeglasses 400. Thus, the sufferer may watch the movie with reduced dry eye symptoms. The dry eye sufferer may detach seals 420 once the movie is finished.

In some embodiments of the invention, seal 420 may be securely attached to frame 405 by stretching seal 420 over a portion of frame 405 surrounding each lens. Seal 420 may be removed by pulling seal 420 from the frame 405. In some other embodiments of the invention, frame 405 may contain an inward groove 490 around each lens 410 between the front face of frame 405 and the rear face of frame 405. The seal 420 may be securely attached to frame 405 by stretching seal 420 over a portion of frame 405 around the inward groove 490 surrounding each lens 410. In some other embodiments of the invention, each seal 420 may be attached to frame 405 using one or more screws, one or more clamps, one or more latches, and so on.

In some embodiments of the invention, seals 420 may attach to glasses which were not originally for use with seals 420. For example, a user may purchase seals 420 and attach the seals to a pair of reading glasses, sunglasses, prescription glasses, and so on. The seals 420 attached to the eyeglasses may create a microenvironment between the eyeglasses, seals 420, and the user to prevent ocular surface abnormalities. As described above, seals 420 may attach to the eyeglasses using one or more screws, one or more clamps, one or more latches, and so on.

Figure 9:
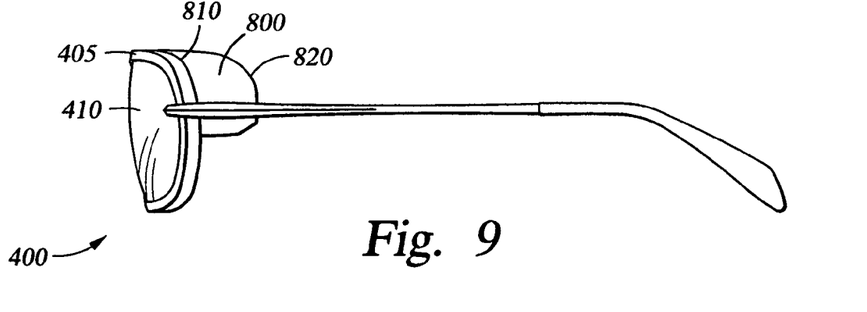
FIG. 9, in accordance with some embodiments of the invention, shows the eyeglasses shown in FIG. 4 containing partially enclosing seals.
Figure 10:
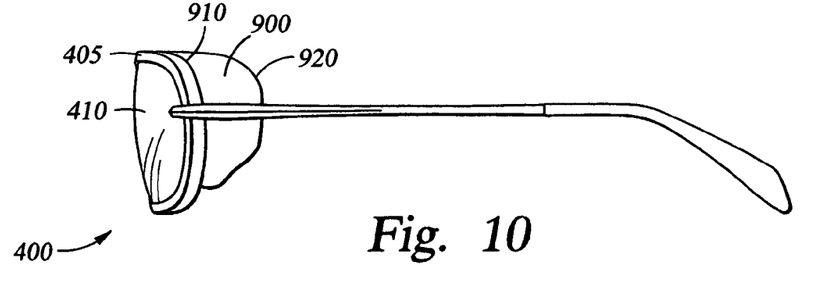
FIG. 10, in accordance with some other embodiments of the invention, shows the eyeglasses shown in FIG. 9 containing seals with a greater degree of enclosure.

Turning now to FIGS. 9 and 10, side views of eyeglasses 400 containing a partially enclosing seal 800/900 is shown. In FIG. 9, partially enclosing seal 800 extends partially down the side of each lens. In some embodiments of the invention, as shown in FIG. 10, partially enclosing seal 900 extends to a greater degree down the side of each lens. A front view and top view of eyeglasses 400 resemble the front view and top view of eyeglasses 400 shown in FIGS. 4 and 6, respectively. Partially enclosing seal 800/900 is attached to frame 405 around part of each lens. Partially enclosing seal 800/900 extends towards a user's face when eyeglasses 400 are worn. The partially enclosing seal 800/900 may be a single continuous piece that extends around the top of each lens 410 and partially down the side of each lens. Partially enclosing seal 800/900 may contain a flexible wall that has an attachment end 810/910 attached to frame 405 and an opposite sealing end 820/920. The length of partially enclosing seal 800/900 is sufficient that substantially all of sealing end 820/920 abuts the user's face when eyeglasses 400 are worn. Thus, eyeglasses 400 form a partially enclosed area about the eyes of the user.

Seal 800/900 may be resilient and capable of molding to the contours of the user's face. Such resiliency and flexibility may be a function of the material properties of the flexible wall or its physical characteristics or design. Seal 800/900 may be made from a flexible material such as plastic, rubber, silicone, foam, leather, a thin, pliable metal, and so on. The shape of partially enclosing seal 800/900 may be adapted to provide flexibility. In some embodiments of the invention, partially enclosing seal 800/900 may be composed of material permeable, semipermeable, or non-permeable to particles.

A microenvironment may exist in the partially enclosed area between lenses 410, frame 405, partially enclosing seal 800/900, and the area around the eyes of the user. Temperature and humidity may increase in the microenvironment in the partially enclosed area about the eyes of the user while the eyeglasses 400 are worn. Increased humidity and temperature may reduce evaporation of aqueous gel layer 210, thereby decreasing the severity and likelihood of dry spots, such as dry spot 310 shown in FIG. 3. Thus, increased temperature and humidity in the area about the eye may reduce ocular surface abnormalities, prevent ocular surface abnormalities, or reduce symptoms of ocular surface abnormalities. The increased temperature and humidity may also improve ocular health.

As described above, partially enclosing eyeglasses 400 shown in FIGS. 8 and 9 may reduce or eliminate ocular discomfort for a user. The eyeglasses 400 may promote airflow in the partially enclosed area between the frame 405, lenses 410, partially enclosed seal 800/900, and the user's eyes while increasing or maintaining humidity and temperature in the partially enclosed area. Eyeglasses 400 shown in FIGS. 9 and 10 may also prevent fogging in lenses 410. Furthermore, the removable seal features, filter features, corrective lens features, tinted lens features, and other features described above may be incorporated into the partially enclosed eyeglasses 400 shown in FIGS. 9 and 10.

Figure 11:
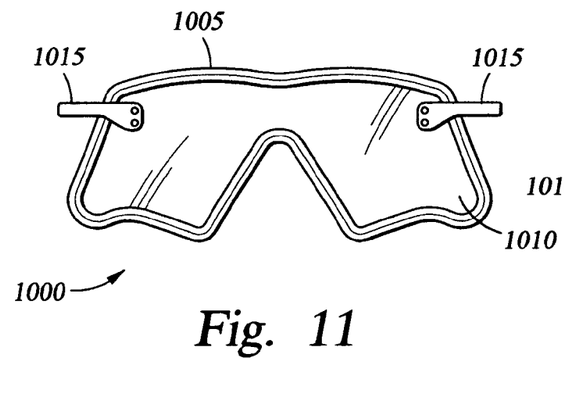
FIG. 11, in accordance with some embodiments of the invention, shows a front view of eyeglasses containing one lens.
Figure 12:
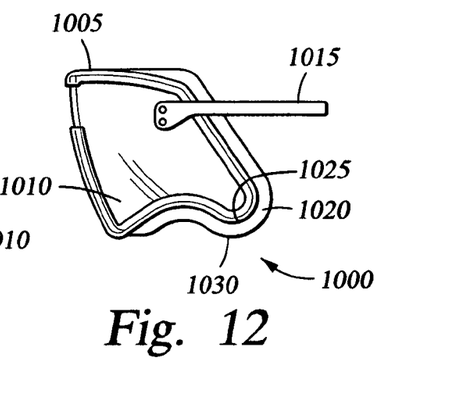
FIG. 12, in accordance with some embodiments of the invention, shows a side view of eyeglasses shown in FIG. 11.
Figure 13:
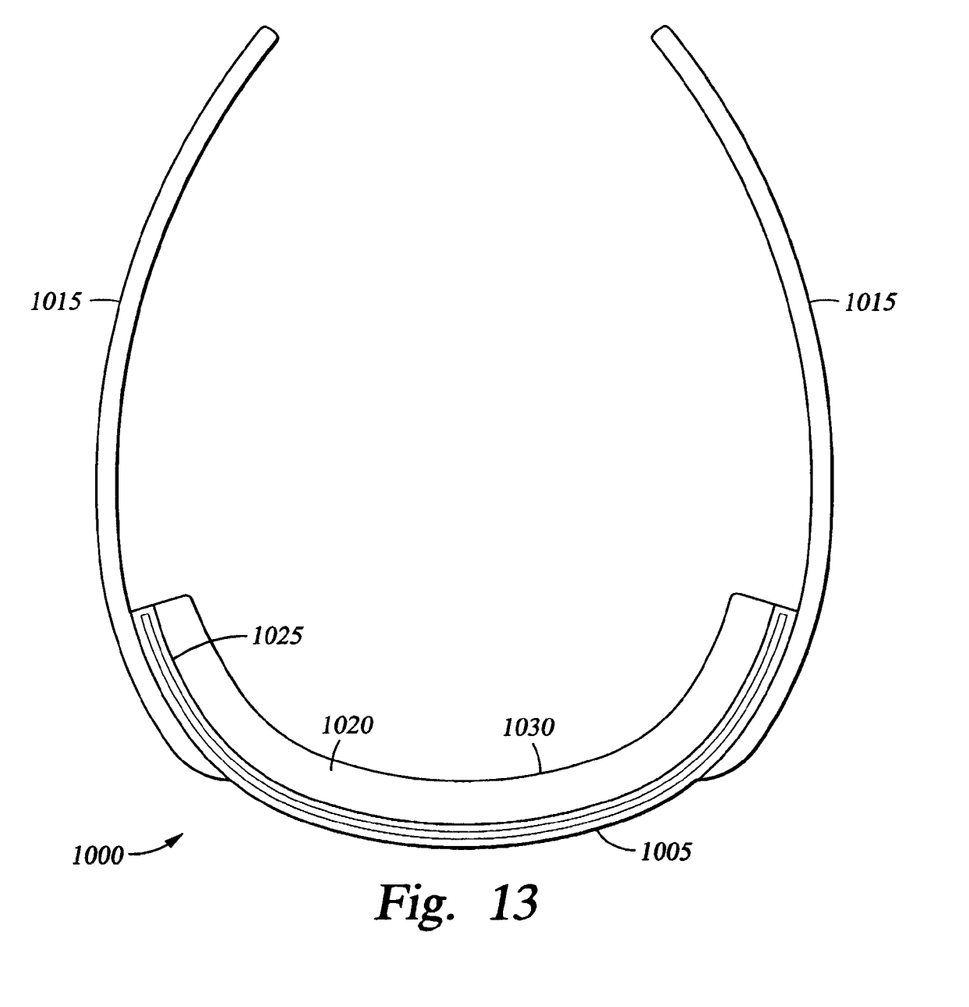

Turning now to FIGS. 11, 12, and 13, a front, side, and top view of eyeglasses 1000 containing a single lens 1010 is shown. Eyeglasses 1000 contain a frame 1005 supporting one lens 1010. Sidearms 1015 attach to frame 1005 and extend away from frame 1005 to support the eyeglasses 1000 on the user's face where the lens 1010 is proximate to the user's eyes. Lens 1010 may be a corrective or non-corrective lens and may also be a bifocal lens, trifocal lens, tinted lens, polarized lens, and so on. Lens 1010 may be glare reducing and may also filter wavelengths of light, such as certain types of ultraviolet light from a display screen or the sun.

A seal 1020 is attached to frame 1005 around lens 1010. Seal 1020 extends towards a users face when eyeglasses 1000 are worn. The seal may be a single continuous piece that extends around the lens. Seal 1020 may contain a flexible wall that has an attachment end 1025 attached to frame 1005 and an opposite sealing end 1030. The length of seal 1020 is sufficient that substantially all of sealing end abuts the user's face when the eyeglasses 1000 are worn to form a seal. Thus, eyeglasses 1000 form an enclosed area about the eyes of a user. In some embodiments of the invention, eyeglasses 1000 may not completely seal to the user's face. Seal 1020 may be resilient and capable of molding to the contours of the user's face. Such resiliency and flexibility may be a function of the material properties of the flexible wall or its physical characteristics or design. Seal 1020 may be made from a flexible material such as plastic, rubber, silicone, foam, leather, or a thin, pliable metal, and so on. The shape of seal 1020 may be adapted to provide flexibility.

In some embodiments of the invention, seal 1020 may be a partially enclosing seal similar to seal 800/900 shown in FIGS. 9 and 10. In some other embodiments of the invention, eyeglasses 1000 may contain one more filters capable of filtering atmosphere entering and exiting the enclosed area between lens 1010, frame 1005, seal 1020, and the user as described above. In some other embodiments, seal 1020 may be removable from and attachable to frame 1005.

A microenvironment may exist in the enclosed area or partially enclosed area between lens 1010, frame 1005, seal 1020, and the area around the eyes of the user. Temperature and humidity may increase in the microenvironment in the enclosed area about the eyes of the user while the eyeglasses 1000 are worn. Increased humidity and temperature may reduce evaporation of aqueous gel layer 210, thereby decreasing the severity and likelihood of dry spots, such as dry spot 310 shown in FIG. 3. Thus, increased temperature and humidity in the area about the eye may reduce ocular surface abnormalities, prevent ocular surface abnormalities, or reduce symptoms of ocular surface abnormalities.

In some embodiments of the invention, the eyeglasses described above may function with a blink indicator capable of reminding a user to blink to maintain an adequate tear film. The blink indicator is disclosed in further detail in U.S. Pat. No. 6,210,000 B1, filed Dec. 22, 1998, and incorporated herein by reference. The blink indicator is also disclosed in more detail in U.S. Pat. No. 6,270,467 B1, filed Apr. 14, 1998, and incorporated herein by reference. The blink indicator generates a blink reminder, such as a light, tone, and so on, to encourage the user to blink. Thus, the user may wear eyeglasses 400 or 1000 and use the blink indicator to maintain an adequate tear film and prevent ocular surface abnormalities. For example, a worker in a factory may focus on a task that slows his blinking rate. The factory worker may wear eyeglasses 400 or 1000 to prevent dust particles or other contaminants from entering his eyes. The factory worker may also use the blink indicator as a reminder to blink. The microenvironment in the eyeglasses in combination with the blink indicator may further reduce ocular surface abnormalities, prevent ocular surface abnormalities, or reduce symptoms of ocular surface abnormalities in the eyes of the user.

The eyeglasses described above may be used by patients who suffer from dry eyes. Additionally, computer users, movie and television watchers, and other users performing concentrated activities may use the eyeglasses to reduce or remove ocular discomforts associated with a lack of blinking. Blepharitis sufferers may also use eyeglasses 400 or 1000 to reduce symptoms of the disorder, such as tear film evaporation. Contact lens users may also use the eyeglasses described above to decrease ocular discomfort. Thus, the eyeglasses described above may relieve or prevent sources or symptoms associated with ocular surface abnormalities. While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A method, comprising:
   providing an area about the eyes of a user that is at least partially enclosed from a surrounding environment, further comprising:
   an eyeglass frame defining at least one lens aperture;
   at least one lens disposed in each lens aperture of the eyeglass frame;
   at least one seal attached to the frame, the at least one seal extending in the general direction of the eyes of the user, wherein the at least one seal is made of a material that is permeable or semipermeable, said material capable of absorbing moisture from the atmosphere and retaining moisture within the area between lens, frame, and seal, wherein the frame, at least one lens, and at least one seal are capable of providing humidity and increasing temperature in an area between the eyes of the user and the at least one lens aperture, wherein the at least one seal further comprises material capable of increasing temperature in the area between the eyes of the user and the at least one lens aperture;
   providing humidity in the area about the eyes of the user.

2. An apparatus, comprising:
an eyeglass frame defining at least one lens aperture, the frame having a front face and a rear face, wherein the rear face is proximate to a user's eyes;
at least one lens disposed in each lens aperture of the eyeglass frame;
at least one seal attached to the frame around at least a portion of the frame, the at least one seal extending from the frame in the direction of the rear face of the frame, wherein the at least one seal is made of a material that is permeable or semipermeable, said material capable of absorbing moisture from the atmosphere and retaining moisture within the area between lens, frame, and seal, wherein the frame, at least one lens, and at least one seal are capable of providing humidity and increasing temperature in an area between the eyes of the user and the at least one lens aperture,
wherein the at least one seal further comprises material capable of increasing temperature in the area between the eyes of the user and the at least one lens aperture.

3. The apparatus of claim 2, wherein the frame, at least one lens, and at least one seal are used for outdoor activity, or watching a screen, or construction work, or operating a vehicle, or riding a bicycle, or participating in a sport, or working in a laboratory, or riding in a vehicle, or any activity in which a reduced rate of blinking occurs.

4. The apparatus of claim 2, wherein the at least one seal is removable from the frame.

5. The apparatus of claim 2, wherein the at least one seal is attached to the frame by at least one screw, or at least one latch, or at least one clamp.

6. The apparatus of claim 2, comprising at least one filter.

7. The apparatus of claim 6, wherein the filter is attached to the frame, or the at least one lens, or the at least one seal.

8. The apparatus of claim 6, wherein the filter is removable and is a high efficiency particle air (HEPA) filter.

9. The apparatus of claim 2, wherein the at least one lens is transparent, or semitransparent, or tinted, or polarized, or operable to filter at least one wavelength of light.

10. The apparatus of claim 2, wherein the at least one lens corrects the user's vision.

11. The apparatus of claim 2, comprising a defogging agent applied to the at least one lens.

12. The apparatus of claim 2, wherein the area between the eyes of the user and the at least one lens aperture is a microenvironment, said microenvironment capable of reducing surface abnormalities in the eyes of the user, and reducing dryness in the eyes of the user, and reducing computer vision syndrome, and reducing ocular discomfort, and improving ocular health.

13. The apparatus of claim 1, wherein the frame, the at least one lens, and the at least one seal form a seal around the user's eyes.

14. The apparatus of claim 1, comprising a nosepiece, said nosepiece attached to the frame proximal to the user's nose when worn, wherein the frame, the at least one lens, the at least one seal, and the nosepiece form a seal around the user's eyes.

15. The apparatus of claim 1, wherein the at least one seal further comprises a flexible wall having an attachment end and an opposing sealing end, wherein the attachment end is attached to the frame, said flexible wall extending from the frame in the direction of the rear face of the frame, said flexible wall and the at least one sealing end adapted to abut the user3 s face when worn.

16. The apparatus of claim 15, wherein the flexible wall is linear between its attachment end and sealing end.

17. The apparatus of claim 15, wherein the flexible wall is an accordion-like shape between its attachment end and sealing end.

18. An apparatus, comprising:
an eyeglass frame defining at least one lens aperture, the frame having a front face and a rear face, wherein the rear face is proximate to a user's eyes;
at least one lens disposed in each lens aperture of the eyeglass frame;
at least one seal, wherein the at least one seal further comprises a flexible wall having an attachment end and an opposing sealing end; and
wherein the attachment end of the at least one seal is operable to attach to at least a portion of the frame, the at least one seal extending from the frame in the direction of the rear face of the frame, wherein the at least one seal is made of a material that is permeable or semipermeable, said material capable of absorbing moisture from the atmosphere and retaining moisture within the area between lens, frame, and seal,
wherein the frame, at least one seal, and at least one lens are capable of providing humidity and increasing temperature in an area between the eyes of the user and the at least one lens aperture, wherein the area between the eyes of the user and the at least one lens aperture is a microenvironment, said microenvironment capable of reducing surface abnormalities in the eyes of the user, and reducing dryness in the eyes of the user, and reducing computer vision syndrome, and reducing ocular discomfort, and improving ocular health.

19. The apparatus of claim 18, wherein the at least one seal is detachable from the frame.

20. The apparatus of claim 18, wherein the frame, at least one seal, and at least one lens define sunglasses, or safety glasses, or prescription glasses, or protective glasses, or lab glasses.

21. The apparatus of claim 18, wherein the at least one seal is attached to the frame by at least one screw, or at least one latch, or at least one clamp.

* * * * *

UNITED STATES PATENT AND TRADEMARK OFFICE
CERTIFICATE OF CORRECTION

| | | |
|---|---|---|
| PATENT NO. | : 7,300,151 B2 | Page 1 of 1 |
| APPLICATION NO. | : 11/216602 | |
| DATED | : November 27, 2007 | |
| INVENTOR(S) | : Richard Yee | |

It is certified that error appears in the above-identified patent and that said Letters Patent is hereby corrected as shown below:

Column 11, line 52, in claim 13, "claim 1" should be changed to --claim 2--.
Column 11, line 55, in claim 14, "claim 1" should be changed to --claim 2--.
Column 12, line 4, in claim 15, "claim 1" should be changed to --claim 2--.
Column 12, line 10, in claim 15, "user3 s" should be changed to --user's--.

Signed and Sealed this

Thirteenth Day of May, 2008

JON W. DUDAS
*Director of the United States Patent and Trademark Office*